United States Patent
Meaney et al.

(10) Patent No.: US 10,113,979 B2
(45) Date of Patent: Oct. 30, 2018

(54) SYSTEMS, PROBES, AND METHODS FOR DIELECTRIC TESTING OF WINE IN BOTTLE

(71) Applicant: The Trustees of Dartmouth College, Hanover, NH (US)

(72) Inventors: Paul M. Meaney, Norwich, VT (US); Timothy Raynolds, Lebanon, NH (US)

(73) Assignee: THE TRUSTEES OF DARTMOUTH COLLEGE, Hanover, NH (US)

( * ) Notice: Subject to any disclaimer, the term of this patent is extended or adjusted under 35 U.S.C. 154(b) by 11 days.

(21) Appl. No.: 15/140,008

(22) Filed: Apr. 27, 2016

(65) Prior Publication Data
US 2016/0313260 A1   Oct. 27, 2016

Related U.S. Application Data

(60) Provisional application No. 62/153,021, filed on Apr. 27, 2015.

(51) Int. Cl.
*G01R 27/04* (2006.01)
*G01R 27/32* (2006.01)
(Continued)

(52) U.S. Cl.
CPC ........... *G01N 22/00* (2013.01); *G01N 33/146* (2013.01); *G01R 27/06* (2013.01); *G01R 27/28* (2013.01);
(Continued)

(58) Field of Classification Search
CPC ........ G01R 27/28; G01R 27/06; G01R 31/11; G01R 27/00; G01R 27/04; G01R 27/32; G01N 22/00
(Continued)

(56) References Cited

U.S. PATENT DOCUMENTS 6,307,156 B1 * 10/2001 Avellanet .............. B21C 37/045
174/128.1
7,339,377 B2   3/2008 Augustine et al.
(Continued)

OTHER PUBLICATIONS

"Agilent 85070E Dielectric Probe Kit: Technical Overview," Agilent Technologies (Santa Clara, CA), Application Note 5989-0222EN, 2014.
(Continued)

*Primary Examiner* — Huy Q Phan
*Assistant Examiner* — Raul Rios Russo
(74) *Attorney, Agent, or Firm* — Lathrop Gage LLP

(57) ABSTRACT

A system for dielectric testing of wine in a bottle includes (a) a coaxial probe for interrogating the wine, wherein the coaxial probe has an open end for contacting an exterior surface of the bottle, and (b) a measurement module for determining a dielectric property associated with the wine by generating and measuring radio waves propagating through the coaxial cable. A method for dielectric testing of wine in a bottle includes measuring a radio-wave reflection signal associated with the wine by interrogating the wine, through the bottle, with radio waves, and determining a dielectric property associated with the wine from the radio-wave reflection signal. A probe for radio-wave interrogation of wine in a bottle has an inner conductor, an outer conductor, and an open end with curvature matching the curvature of an exterior surface of the bottle.

9 Claims, 8 Drawing Sheets

(51) Int. Cl.
| | |
|---|---|
| G01N 22/00 | (2006.01) |
| G01N 33/14 | (2006.01) |
| G01R 27/28 | (2006.01) |
| G01R 31/11 | (2006.01) |
| G01R 27/06 | (2006.01) |
| G01R 27/00 | (2006.01) |

(52) U.S. Cl.
CPC .............. *G01R 31/11* (2013.01); *G01R 27/00* (2013.01); *G01R 27/04* (2013.01); *G01R 27/32* (2013.01)

(58) Field of Classification Search
USPC ... 324/600, 76.11–76.83, 459, 629, 637, 642
See application file for complete search history.

(56) References Cited

U.S. PATENT DOCUMENTS

| | | | | |
|---|---|---|---|---|
| 2002/0053446 | A1* | 5/2002 | Moe | H01B 11/1804 174/21 C |
| 2005/0009566 | A1* | 1/2005 | Kaegebein | H01Q 1/1207 455/562.1 |
| 2009/0212881 | A1* | 8/2009 | Snodgrass | H01P 5/085 333/33 |
| 2010/0071929 | A1* | 3/2010 | Hesselbarth | H01B 11/1839 174/113 R |
| 2010/0117757 | A1* | 5/2010 | Yano | H01P 5/103 333/27 |
| 2010/0212926 | A1* | 8/2010 | Cho | H01B 11/1878 174/28 |
| 2011/0184681 | A1 | 7/2011 | Augustine et al. | |
| 2013/0005180 | A1* | 1/2013 | Malloy | H01R 9/0524 439/578 |
| 2013/0038410 | A1* | 2/2013 | Van Swearingen | H01P 3/06 333/238 |
| 2014/0290830 | A1* | 10/2014 | Brannan | A61B 18/1815 156/86 |

OTHER PUBLICATIONS

"Basics of measuring the dielectric properties of materials," Agilent Technologies (Santa Clara, CA), Application Note 5989-2589EN, 2014.
Agilent Technologies (2004), "Microwave Dielectric Spectroscopy Workshop, Measure the Difference".
Alanen et al. (1998), "Measurement of dielectric properties of subcutaneous fat with open-ended coaxial sensors," Physics in Medicine and Biology, vol. 43, pp. 475-485, 1998.
Alanen et al. (Oct. 1998), "Variational Formulation of Open-Ended Coaxial Line in Contact with Layered Biological Medium," IEEE Transactions on Biomedical Engineering, vol. 45, No. 10, 1241-1248, Oct. 1998.
Anderson et al. (1994) S, "Dielectric measurements using a rational function model," IEEE Transactions on Microwave Theory and Techniques vol. 42, pp. 199-204, 1994.
Athey et al. (1982), "Measurement of radio frequency permittivity of biological tissue with an open-ended coaxial line: Part 1," IEEE Transactions on Microwave Theory and techniques, vol. 30, pp. 82-86, 1982.
Birkballe et al. (Aug. 2013), "Can tissue dielectric constant measurement aid in differentiating lymphoedema from lipoedema in women with swollen legs?" British Journal of Dermatology, epub, Aug. 2013.
Boughriet et al. (1999), "The Measurement of Dielectric Properties of Liquids at Microwave Frequencies Using Open-ended Coaxial Probes," 1st World Congress on Industrial Process Tomography, Buxton, Greater Manchester, Apr. 14-17, 1999.
Chan et al. (1992), "Modeling of the reflection coefficient of an open ended coaxial line and its use for accurate complex permittivity measurements at frequencies up to 20 GHz," IEEE International Conference on Dielectric Materials, Measurements and Applications vol. 1992, pp. 366-369, 1992.
Chaudhary et al. (1984), "Dielectric properties of normal and malignant human breast tissues at radiowave and microwave frequencies," Indian J Biochem Bio, vol. 21, pp. 76-79, 1984.
Cook et al. (1974), "The properties of water in biological systems," Annual Review of Biophysics and Bioengineering, vol. 3, pp. 95-126, 1974.
Delfin Technologies, MoistureMeterD, http://www.delfintech.com/en/moisturemeterd/.
Foster et al. (1981), "Dielectric properties of tumor and normal tissues at radio through microwave frequencies," Journal of Microwave Power, vol. 16, pp. 107-119, 1981.
Fricke (1924), "A mathematical treatment of the electrical conductivity and capacity of disperse systems," Phys. Rev., vol. 24, pp. 575-587, 1924.
Gabriel et al. (1994) "Admittance models for open ended coaxial probes and their place in dielectric spectroscopy," Physics in Medicine and Biology, vol. 39, pp. 2183-2200, 1994.
Gabriel et al. (1996), "The dielectric properties of biological tissues: III. Parametric models for the dielectric spectrum of tissues," Physics in Medicine and Biology, vol. 41, pp. 2271-2293, 1996.
Gabriel et al. (1996), "The dielectric properties of biological tissues: I. literature survey," Physics in Medicine and Biology, vol. 41, pp. 2231-2249, 1996.
Gabriel et al. (1996), "The dielectric properties of biological tissues: II. Measurements in the frequency range 10 Hz to 20 GHz," Physics in Medicine and Biology, vol. 41, pp. 2251-2269, 1996.
Gajda et al. (1983), "Numerical analysis of open-ended coaxial lines," IEEE Transactions on Microwave Theory and Techniques, vol. 31, pp. 380-384, 1983.
Grant et al. (1989), "A critical study of the open-ended coaxial line sensor technique for RF and microwave complex permittivity measurements," Journal of Physics E: Scientific Instrumentation, vol. 1989, pp. 757-770, 1989.
Guihan et al. (2012), "Assessing the feasibility of subepidermal moisture to predict erythema and stage 1 pressure ulcers in persons with spinal cord injury: A pilot study," Journal of Spinal Cord Medicine, vol. 35, pp. 46-52, 2012.
Hagl et al. (2003), "Sensing volume of open-ended coaxial probes for dielectric characterization of breast tissue at microwave frequencies," IEEE Transactions on Microwave Theory and Techniques, vol. 51, pp. 1194-1206, 2003.
Joines et al. (1994), "The measured electrical properties of normal and malignant human tissue from 50 to 900 MHz," Medical Physics, vol. 41, pp. 547-550, 1994.
Keysight Technologies (Jan. 2015), "Basics of Measuring the Dielectric Properties of Materials".
Kitchin et al. (1981), "Detection of Methanol in Wine by Microwave Spectroscopy," Anal. Chem. 1981, 53, 1190-1192.
Klemm et al. (2008), "Experimental and clinical results of breast cancer detection using UWB microwave radar," IEEE Antennas and Propagation International Symposium, San Diego, CA, pp. 1-4, 2008.
Lazebnik et al. (2007), "A large-scale study of the ultrawideband microwave dielectric properties of normal breast tissue obtained from reduction surgeries," Physics in Medicine and Biology, vol. 52, pp. 2637-2656, 2007.
Lazebnik et al. (2007), "A large-scale tissues obtained from cancer surgeries," Physics in Medicine and Biology, vol. 52, pp. 6093-6115, 2007.
Mayrovitz et al. (2008), "Local tissue water assessed by tissue dielectric constant: anatomical site and depth dependence in women prior to breast cancer treatment-related surgery," Clin Physiol Imaging, vol. 28, pp. 337-342, 2008.
Meaney et al. (2013), "Integration of a microwave tomographic imaging system with MR for improved breast imaging," Medical Physics, vol. 40, pp. 103101-1-103101-13, 2013.
Meaney et al. (2014), "Microwave open-ended coaxial dielectric probe: interpretation of the sensing volume re-visited," BMC Medical Physics, vol. 14, paper # 1756-6649 2014.

(56) References Cited

OTHER PUBLICATIONS

Nelson (2010), "Fundamentals of dielectric properties measurements and agricultural applications," Journal of Microwave Power and Electromagnetic Energy, vol. 44, pp. 98-113, 2010.
Olmi et al. (Nov. 2007), "Monitoring Alcoholic Fermentation by Microwave Dielectric Spectroscopy," Journal of Microwave Power & Electromagnetic Energy vol. 41, No. 3, 2007.
Poplack et al. (2007), "Electromagnetic breast imaging: pilot results in women with abnormal mammography," Radiology, vol. 243, pp. 350-359, 2007.
Schepps et al. (1980), The UHF and microwave dielectric properties of normal and tumor tissues: variation in dielectric properties with tissue water content, Physics in Medicine and Biology, vol. 25, pp. 1149-1159, 1980.
Schwan (1957), "Electrical properties of tissue and cell suspensions," Advances in Biological and Medical Physics, vol. 5, pp. 147-209, 1957.
Schwan (1963), "The determination of biological impedances," Physical Techniques in Biological Research, vol. 6, pp. 323-407, 1963.
Schwan et al. (1977), "Microwave dielectric properties of tissue: some comments on the rotational mobility of tissue water," Biophysical Journal, vol. 17, pp. 193-197, 1977.
Stuchly et al. (1980), "Coaxial line reflection method for measuring dielectric properties of biological substances at radio and microwave frequencies—a review," IEEE Transactions on Instrumentation Measurements, vol. 29, pp. 176-183, 1980.
Surowiec et al. (1988), "Dielectric properties of breast carcinoma and the surrounding tissues," IEEE Transactions on Biomedical Engineering, 1988, vol. 35, pp. 257-263, 1988.
Times Microwave Systems, LMR®-1700 Flexible Low Loss Communications Coax.

* cited by examiner

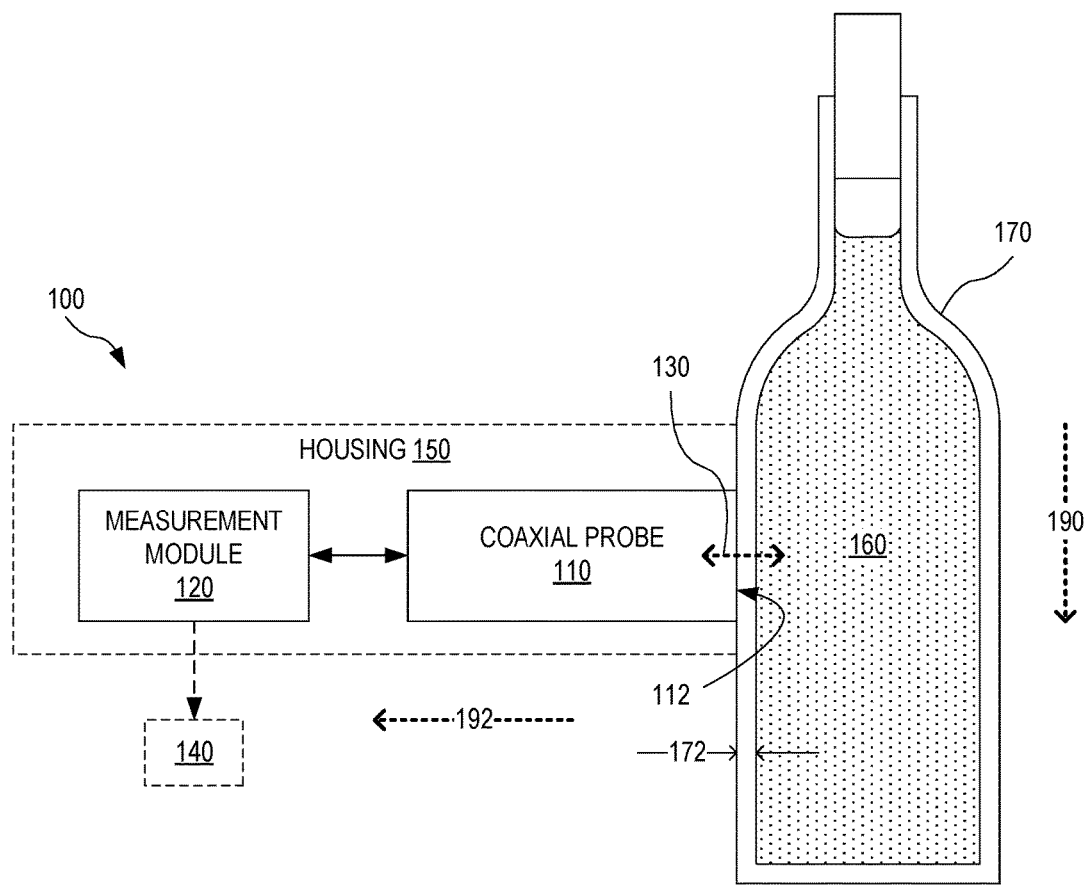
FIG. 1
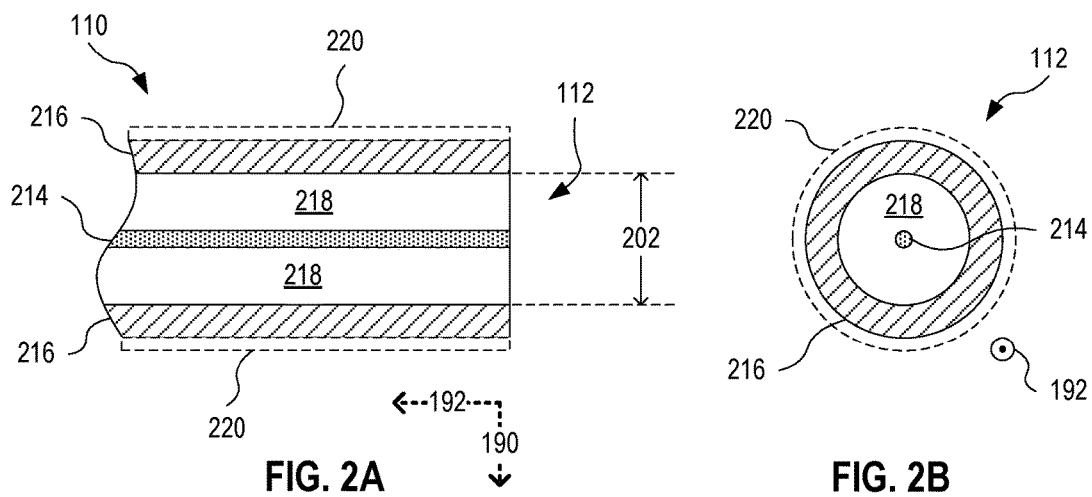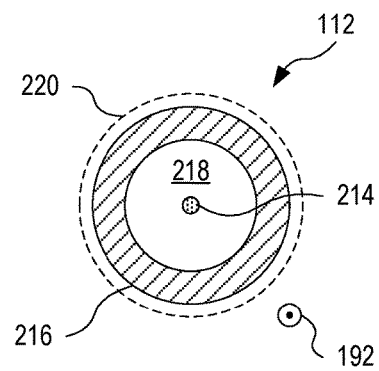
FIG. 2A  FIG. 2B

```
                                    300
                                      ↘

┌──────────────────────────────────────────────────────────────────────┐
│   MEASURE RADIO WAVE REFLECTION PROPERTY OF ASSOCIATED WITH WINE     │
│                               310                                     │
│   ┌──────────────────────────────────────────────────────────────┐   │
│   │   INTERROGATE WINE, THROUGH BOTTLE, WITH RADIO WAVES         │   │
│   │                          312                                  │   │
│   └──────────────────────────────────────────────────────────────┘   │
└──────────────────────────────────────────────────────────────────────┘
                                      │
                                      ▼
┌──────────────────────────────────────────────────────────────────────┐
│   DETERMINE DIELECTRIC PROPERTY ASSOCIATED WITH WINE FROM RADIO      │
│                      WAVE REFLECTION PROPERTY                         │
│                               320                                     │
└──────────────────────────────────────────────────────────────────────┘
                                      ┆
                                      ▼
┌ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┐
    OUTPUT DIELECTRIC PROPERTY ASSOCIATED WITH WINE
│                              330                                      │
└ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┘
```

FIG. 3

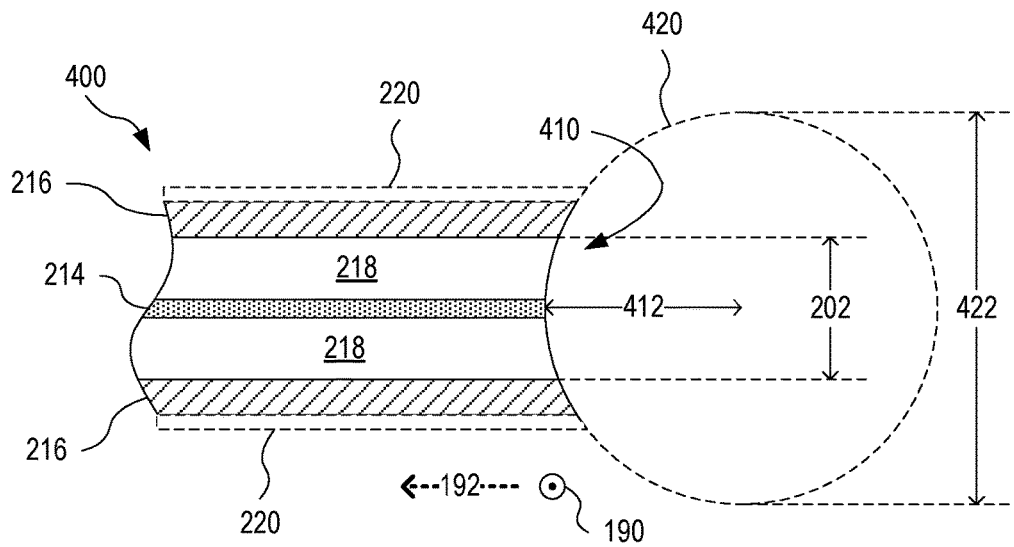

FIG. 4

SYSTEMS, PROBES, AND METHODS FOR DIELECTRIC TESTING OF WINE IN BOTTLE

CROSS-REFERENCE TO RELATED APPLICATIONS

The present application claims the benefit of priority from U.S. Provisional Application Ser. No. 62/153,021 filed Apr. 27, 2015, which is incorporated herein by reference in its entirety.

BACKGROUND

Wine testing is used at wine production facilities, and also at higher-end restaurants and by individual wine enthusiasts. However, conventional wine testing methods generally require direct access to the wine and cannot be performed on wine inside closed bottles. Thus, for wine that has already been bottled, such conventional wine testing is necessarily invasive.

One prior art method for non-invasive testing of wine in bottles utilizes nuclear magnetic resonance (NMR) spectroscopy to at least partly characterize the chemical composition of the wine. The NMR instrument is very expensive and large. Therefore, the NMR approach is not well-suited for small-scale wine testing at decentralized locations by restaurants, wine shops, or consumers.

Another prior art method uses a radio-frequency coil to measure dielectric properties of wine in bottles. The coil encircles the bottle and cooperates with electronics equipment to detect changes in the inherent resonance frequency of the wine at frequencies below 30 megahertz (MHz). This method requires significant electronics equipment. The interface with the bottle, e.g., the radio-frequency coil, must be large in order to encircle the bottle. In addition, wine bottle labels commonly have metallic print that interferes with the measurements and is likely to cause the measurement to fail.

SUMMARY

In an embodiment, a system for dielectric testing of wine in a bottle, includes a coaxial probe for interrogating the wine. The coaxial probe has an open end for contacting an exterior surface of the bottle. The system further includes a measurement module for determining a dielectric property associated with the wine by generating and measuring radio waves propagating through the coaxial cable.

In an embodiment, a method for dielectric testing of wine in a bottle, includes measuring a radio-wave reflection signal associated with the wine by interrogating the wine, through the bottle, with radio waves. The method further includes determining a dielectric property associated with the wine from the radio-wave reflection signal.

In an embodiment, a probe for radio-wave interrogation of wine in a bottle has an inner conductor, an outer conductor, and an open end. The outer conductor is coaxial with the inner conductor and spaced apart from the inner conductor by a dielectric material. The open end includes an end face of the inner conductor and an end face of the outer conductor. In addition, the open end has curvature matching the curvature of an exterior surface of the bottle.

BRIEF DESCRIPTION OF THE DRAWINGS

FIG. 1 illustrates a system for dielectric testing of wine in a bottle, according to an embodiment.

FIGS. 2A and 2B illustrate an open-ended coaxial probe for radio-wave interrogation of wine in a bottle, according to an embodiment.

FIG. 3 illustrates a method for dielectric testing of wine in a bottle, according to an embodiment.

FIG. 4 illustrates an open-ended coaxial probe, for radio-wave interrogation of wine through a bottle, which has a cylindrically curved open end, according to an embodiment.

DETAILED DESCRIPTION OF THE EMBODIMENTS

Figure 5:
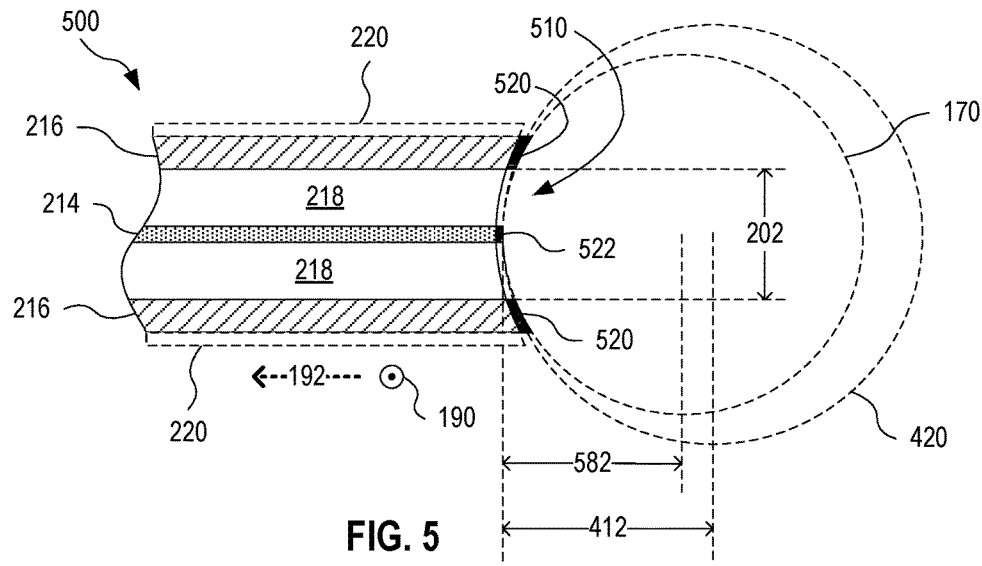
FIG. 5 illustrates an open-ended coaxial probe, for radio-wave interrogation of wine through a bottle, which has a cylindrically curved open end that includes a deformable, conductive gasket, according to an embodiment.

FIG. 1 illustrates one exemplary system 100 for dielectric testing of wine 160 in a bottle 170. System 100 uses radio waves 130 to interrogate wine 160 through bottle 170 to determine at least one dielectric property 140 associated with wine 160. System 100 allows for non-invasive testing of wine 160 in that testing of wine 160 by system 100 does not require opening bottle 170.

Herein, a "dielectric property" refers to a permittivity value such as the complex relative permittivity, the real part of the relative permittivity, the imaginary part of the relative permittivity, or a combination or derivative thereof; and "dielectric constant" and "real relative permittivity" each refer to the real part of the relative permittivity. All of the complex relative permittivity, the real part of the relative permittivity, the imaginary part of the relative permittivity, and the dielectric constant may be frequency-dependent. Herein, "wine" generally refers to an alcoholic beverage made from fermented grapes and/or other fruit. However, it is understood that the presently disclosed systems, probes, and methods are readily extended to other beverages such as other alcoholic drinks.

The dielectric properties of wine 160 are a function of the material composition of wine 160. For illustration, at frequencies up to about one gigahertz (GHz), the dielectric constant of water ranges from 77 to 88. At these frequencies, the dielectric constants of non-polar liquids, such as oils, are in the range between 2 and 5. The dielectric constant of different alcohols fall in the range between non-polar liquids and water, with the exact value depending on the proportion of non-polar to polar portions of the molecules. For example, the dielectric constants of ethanol (two carbon atoms), propanol (three carbon atoms), and butanol (four carbon atoms) are approximately 24, 22, and 18, respectively. In addition, the relaxation frequencies of these partially polar molecules shift downward with decreasing polarity. The dielectric properties exhibit unique characteristics near the relaxation frequencies. Without being bound by theory, the real part of the relative permittivity generally decreases at a relaxation frequency while the imaginary part of the relative permittivity peaks at the relaxation frequency. Such relaxation frequencies are a function of the material composition of wine 160. Accordingly, dielectric properties of wine 160 may provide information about the material composition of wine 160. In one exemplary scenario, an amount of ethanol in wine 160 oxidizes into acetic acid (vinegar). At frequencies below about one GHz, the dielectric constant of acetic acid is about 6, which is significantly lower than the dielectric constant of ethanol. Hence, determination of the dielectric constant of wine 160 may indicate if undesirable oxidation of ethanol into acetic acid has taken place.

System 100 includes an open-ended coaxial probe 110 and a measurement module 120. Coaxial probe 110 has an open end 112 through which system 100 interrogates wine 160. FIGS. 2A and 2B show coaxial probe 110 in further detail. FIG. 3 illustrates one exemplary method 300 for dielectric testing of wine 160 in bottle 170. FIGS. 1, 2A, 2B, and 3 are best viewed together.

Critical to the performance of system 100 is that (a) coaxial probe 110 has a large diameter that exceeds the diameter of conventional coaxial probes by about an order of magnitude or more, and (b) open end 112 is shaped to at least approximately match the shape of bottle 170. The large diameter of coaxial probe 110 ensures that radio waves 130 have penetration depth sufficient to pass through bottle 170 into wine 160. In contrast, the penetration depth of a conventional coaxial probe is insufficient to reach wine 160 through bottle 170. Conventionally, large diameter coaxial probes are viewed as being less attractive since the frequency, at which propagation of radio waves through a coaxial probe fails, decreases with increasing diameter. However, as is shown in the present disclosure, the diameter of coaxial probe 110, required for penetration of radio waves 130 into wine 160 through bottle 170, allows for interrogation of wine 160 at frequencies sufficiently high to determine an informative dielectric property 140 for wine 160. The shape of open end 112 eliminates or reduces any air gap between coaxial probe 112 and bottle 170. If present, such an air gap may greatly affect the measurements and in worst case preclude the determination of dielectric property 140.

FIG. 2A shows open-ended coaxial probe 110 in cross-sectional side view, wherein the cross section is taken in the plane spanned by directions 190 and 192 indicated in FIG. 1. Direction 190 is along the height of bottle 170 and direction 192 is along the general propagation direction of radio waves 130 through coaxial probe 110. FIG. 2B shows open end 112 in a view along direction 192.

Coaxial probe 110 includes an inner conductor 214, and outer conductor 216, and open end 112. Open end 112 includes an end face of inner conductor 214 and an end face of outer conductor 216. Inner conductor 214 and outer conductor 216 are spaced apart by a dielectric insulator 218. Dielectric insulator 218 is, for example, plastic, foam plastic, air (or other gaseous medium) with spacers supporting inner conductor 214, and/or a combination thereof. In certain embodiments, dielectric insulator 218 is composed essentially of solid polyethylene, polytetrafluoroethylene, and/or a derivative thereof. Inner conductor 214 and outer conductor 216 are, for example, made of (a) metal such as copper, (b) metal plated with another metal, such as silver-plated copper, or (c) metal-plated dielectric such as copper-plated plastic. Either or both of inner conductor 214 and outer conductor 216 may be a metal wire mesh. Optionally, coaxial probe 110 further includes an insulating jacket 220. Insulating jacket 220 may include a plastic such as polyvinyl chloride (PVC) or another polymer.

Outer conductor 216 has an inner diameter 202. The penetration depth of radio waves 130 away from open end 112 into bottle 170 and wine 160 is an increasing function of inner diameter 202. A typical example of bottle 170 has wall-thickness 172 in the range from 2.0 to 3.5 millimeters. Inner diameter 202 is sufficiently large that the penetration depth of radio waves 130 away from open end 112 exceeds wall-thickness 172. In one embodiment, inner diameter 202 is two inches, which leads to a penetration depth of approximately four millimeters. In another embodiment, inner diameter 202 is at least fifty millimeters, leading to a penetration depth of approximately 3.7 millimeters or more. In yet another embodiment, inner diameter 202 is at least 30 millimeters, leading to a penetration depth of approximately 2.5 millimeters or more. In a further embodiment, inner diameter 202 is sufficiently large that the penetration depth is at least three millimeters. For comparison, in conventional coaxial probes, the inner diameter of the outer conductor is generally about a tenth of an inch or less, which is insufficient for interrogation of wine 160 through bottle 170.

Without departing from the scope hereof, inner conductor 214 and outer conductor 216 need not be coaxial. For example, inner conductor 214 may be shifted away from the axis of outer conductor 216 by a small amount. Also without departing from the scope hereof, the shape of inner conductor 214 and/or outer conductor 216 may deviate from the circular cross section shown in FIG. 2B. For example, the cross section of inner conductor 214 and/or outer conductor 216 may be rectangular.

In a step 310 of method 300, system 100 measures a radio-wave reflection signal associated with wine 160. Step 310 includes a step 312 of interrogating wine 160 through bottle 170. In step 310, measurement module 120 generates radio waves 130, couples radio waves 130 to coaxial probe 110, and measures a radio-wave reflection signal of radio waves 130 travelling through coaxial probe 110 and interacting with wine 160 through bottle 170 at open end 112. This radio-wave reflection signal depends on the dielectric properties of media, with which radio waves 130 interact externally to open end 112. Hence, the radio-wave reflection signal depends on the dielectric properties of wine 160, bottle 170, and, if applicable, any other media located between open end 112 and wine 160 such as an air gap.

In one embodiment, radio waves 130 are of a single frequency in the range between 10 MHz and 2 GHz. In another embodiment, radio waves 130 are of a single frequency in the range between 50 and 300 MHz. In yet another embodiment, radio waves 130 includes radio waves of multiple different frequencies in the range between 10 MHz and 2 GHz or in the range between 50 and 300 MHz. In a further embodiment, the frequency of radio waves 130 is scanned over a range that includes the range between 50 and 300 MHz or the range between 10 MHz and 1 GHz.

The portion of bottle 170 located between open end 112 and wine 160, and thus interacting with radio waves 130, may be made of any electrically insulating material. Exemplary materials for this portion of bottle 170 include glass, plastic, and paper. Without departing from the scope hereof, this portion of bottle 170 may include a label. If bottle 170 includes a label with metallic paint, step 310 is advantageously performed with open end 112 located at a portion of bottle 170 that is away from the metallic paint.

In a step 320, measurement module 120 determines, based upon the radio-wave reflection signal measured in step 310, a dielectric property 140 associated with wine 160. In one embodiment, dielectric property 140 is a composite dielectric property of wine 160, bottle 170, and any other intervening media between open end 112 and wine 160. In another embodiment, dielectric property 140 is a dielectric property of wine 160 alone. Measurement module 120 may utilize methods known in the art to determine dielectric property 140 from the radio-wave reflection signal measured in step 310.

In an optional step 330, measurement module 120 outputs dielectric property 140. In one example, measurement module 120 includes a display for displaying dielectric property 140. In another example, measurement module 120 outputs dielectric property 140 to a system external to system 100, such as an external computer system. In yet another example, measurement module 120 stores dielectric property 140 to a data storage not shown in FIG. 1. Such a data storage may be implemented within system 100 or externally to system 100.

In certain embodiments, system 100 includes a housing 150 that contains measurement module 120 and coaxial probe 110. Housing 150 includes an opening through which coaxial probe 110 interrogates wine 160 with radio waves 130. In one implementation, system 100 is a handheld device, and a user may take advantage of mobility of system 100 to test multiple bottles of wine at different locations. In another implementation, system 100 is a larger instrument suited for use in a stationary location. In one such implementation, system 100 is placed at a conveyer belt at production, shipping, and/or packaging facility. In yet another implementation, coaxial probe 110 is a handheld device communicatively coupled with measurement module 120.

FIG. 4 illustrates one exemplary open-ended coaxial probe 400 having a cylindrically curved open end 410 for radio-wave interrogation of wine 160 in bottle 170 with minimal air gap between open end 410 and a substantially cylindrically shaped portion of bottle 170. The radio-wave reflection signal measured in step 310 of method 300 (FIG. 3) may be influenced by media located between bottle 170 and the coaxial probe (e.g., coaxial probe 110 or 400). For example, the relative permittivity of air is close to 1.0, which is very different from the relative permittivity of components of wine 160. Therefore, it is advantageous to minimize the contribution from such intervening media. Cylindrically curved open end 410 is shaped to reduce or eliminate any gap between curved open end 410 and bottle 170.

Coaxial probe 400 is an embodiment of coaxial probe 110 (FIG. 1), implemented with cylindrically curved open end 410. Cylindrically curved open end 410 is an embodiment of open end 112. FIG. 4 shows coaxial probe 400 in cross-sectional view along direction 190. Cylindrically curved open end 410 is configured to match the shape of a cylinder 420 having cylinder axis along direction 190. Cylindrically curved open end 410 has radius of curvature 412 equaling the radius of cylinder 420.

In one implementation, cylinder 420 indicates a substantially cylindrically shaped portion of bottle 170, and radius of curvature 412 is half (or approximately half) the value of diameter 422 of the substantially cylindrically shaped portion of bottle 170. In one exemplary scenario, diameter 422 is around three inches and radius of curvature 412 is around 1.5 inches. For example, radius of curvature 412 is in the range between 1.3 and 1.7 inches to approximately match the shape of a typical wine bottle.

Without departing from the scope hereof, open end 410 may be curved to match a shape that deviates from being cylindrical. For example, open end 410 may be curved to match a shape having oval cross section in the plane orthogonal to direction 190.

FIG. 5 illustrates one exemplary open-ended coaxial probe 500 having a cylindrically curved open end 510 that includes a deformable, conductive gasket 520 for ensuring, or at least improving, reliability of electrical contact between open end 510 and bottle 170 (FIG. 1). Coaxial probe 500 is an embodiment of coaxial probe 110, and is similar to coaxial probe 400 (FIG. 4) except for further including deformable, conductive gasket 520. Open end 510 is an embodiment of open end 112. FIG. 5 shows coaxial probe 500 in cross-sectional view along direction 190.

Deformable, conductive gasket 520 is located at outer conductor 216 and thus serves to provide a deformable extension of outer conductor 216. By virtue of deformable, conductive gasket 520, coaxial probe 500 may form reliable electrical contact with bottle 170 for a wider range of bottle diameters and shapes. Additionally, deformable, conductive gasket 520 may serve to avoid or reduce repeatability issues associated with an air gap between outer conductor 216 and bottle 170. In the exemplary scenario shown in FIG. 5, coaxial probe 500 (in the absence of deformable, conductive gasket 520) has radius of curvature 412. However, the corresponding radius 582 of bottle 170 is less than radius of curvature 412. Deformable, conductive gasket 520 ensures reliable electrical contact between outer conductor 216 and bottle 170 despite the discrepancy between radius of curvature 412 and radius 582.

In an embodiment, open end 510 further includes a deformable, conductive gasket 522 at inner conductor 214. Deformable, conductive gasket 522 ensures, or at least improves, reliable electrical contact between inner conductor 214 and bottle 170, and thus provides benefits similar to that of deformable, conductive gasket 520.

Without departing from the scope hereof, other embodiments of coaxial probe 110 may be modified in a similar fashion as shown in FIG. 5 to include at least one deformable, conductive gasket. For example, at least one deformable, conductive gasket may be incorporated in an open end of coaxial probe 110, coaxial probe 600 (see FIGS. 6A and 6B discussed below), and/or coaxial probe 1000 (see FIG. 10 discussed below).

Figure 6A:
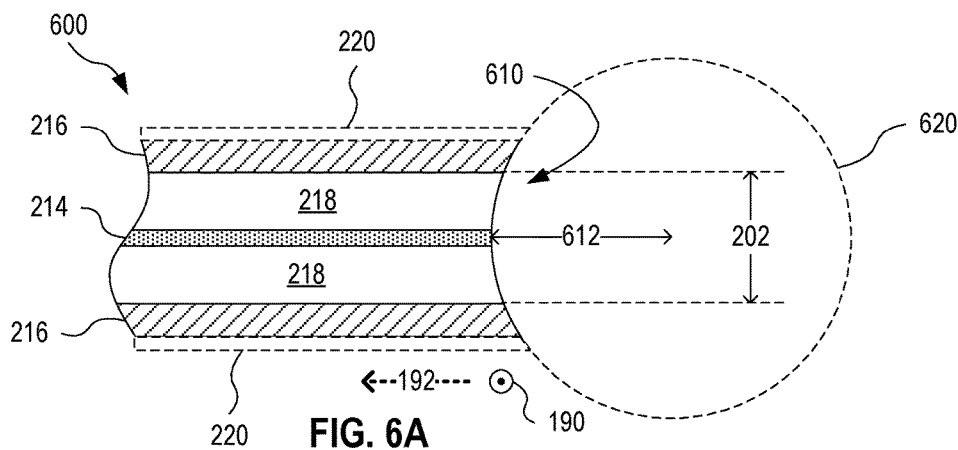
FIGS. 6A and 6B illustrate an open-ended coaxial probe, for radio-wave interrogation of wine through a bottle, which has a curved open end with three-dimensional curvature, according to an embodiment.
Figure 6B:
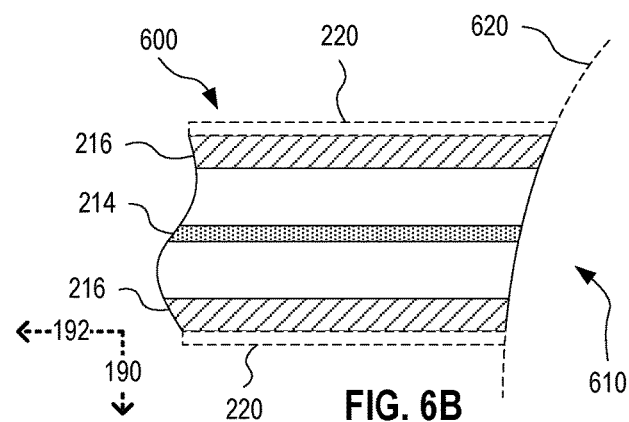

FIGS. 6A and 6B illustrate one exemplary open-ended coaxial probe 600 having a curved open end 610 with three-dimensional curvature to at least approximately match the shape of a bottle 170 (FIG. 1) having three-dimensional curvature. FIG. 6A shows coaxial probe 600 in cross-sectional view along direction 190. FIG. 6B shows coaxial probe 600 in cross-sectional view, wherein the cross section is within the plane spanned by directions 190 and 192. Coaxial probe 600 is an embodiment of coaxial probe 110, and open end 610 is an embodiment of open end 112.

Coaxial probe 600 is similar to coaxial probe 400 (FIG. 4) and extends the benefits of coaxial probe 400 to three-dimensionally curved portions of bottle 170. At every position of coaxial probe 400 along direction 190, open end 610 has radius of curvature 612 to match a shape 620 that, at every location of open end 610 along direction 190, is substantially circular in the plane orthogonal to direction 190 (see FIG. 6A). In addition, as seen in FIG. 6B, open end 610 is curved such that radius of curvature 612 varies with the location along direction 190. As a result, open end 610 is shaped to match a three-dimensionally curved portion of bottle 170. In the exemplary scenario shown in FIGS. 6A and 6B, shape 620 corresponds to a portion of bottle 170 having larger diameter closer to the bottom of bottle 170 and smaller diameter closer to the neck of bottle 170.

Figure 7:
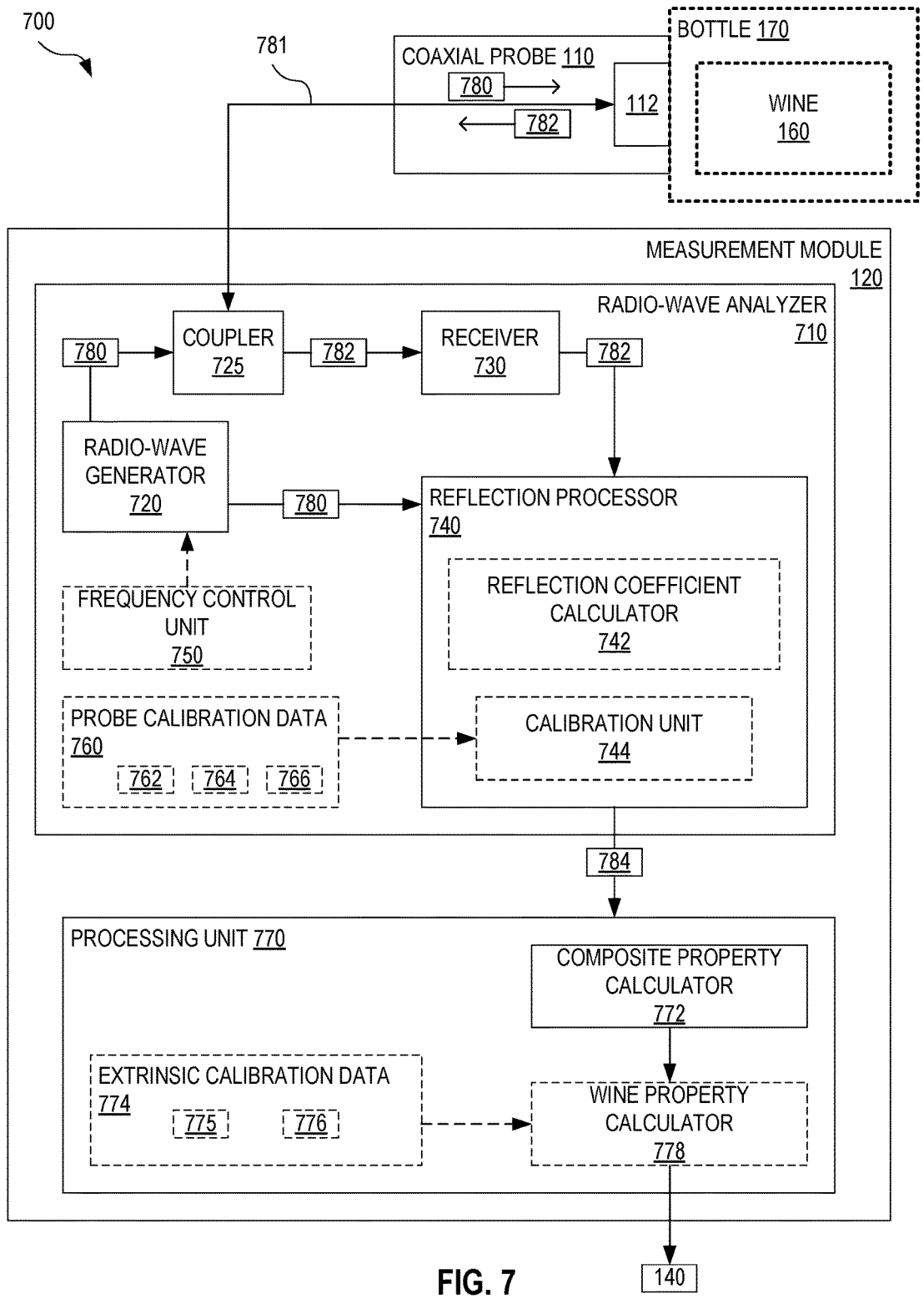
FIG. 7 illustrates another system for dielectric testing of wine in a bottle, according to an embodiment.

FIG. 7 illustrates one exemplary system 700 for dielectric testing of wine 160 in bottle 170. System 700 is an embodiment of system 100 (FIG. 1), wherein measurement module 120 is implemented with a radio-wave analyzer 710 and a processing unit 770. Radio-wave analyzer 710 cooperates with coaxial probe 110 to measure a radio wave reflection signal 784 associated with wine 160. Processing unit 770 processes radio wave reflection signal 784 to determine dielectric property 140 associated with wine 160. System 700 may implement coaxial probe 110 according to one of the embodiments shown in FIG. 2A, 2B, 4, 5, 6A, 6B, or 10.

Radio-wave analyzer 710 includes a radio-wave generator 720 that generates input radio waves 780 and couples input radio waves 780 to coaxial probe 110. Radio-wave analyzer 710 also includes a receiver 730 that detects reflected radio waves 782. Reflected radio waves 782 are the reflection of input radio waves 780 formed at open end 112 of coaxial probe 110. Input radio waves 780 and reflected radio waves 782 together form an example of radio waves 130. Radio-wave analyzer 710 includes a coupler 725 that (a) directs input radio waves 780 from radio-wave generator 720 to coaxial probe 110 and (b) directs reflected radio waves 782 from coaxial probe 110 to receiver 730, such that input radio waves 780 and reflected radio waves 782 propagate along the same transmission line 781 when external to radio-wave analyzer 710. In addition, radio-wave analyzer 710 includes a reflection processor 740 that is communicatively coupled with radio-wave generator 720 and receiver 730. Reflection processor 740 processes input radio waves 780 (or associated data) and reflected radio waves 782 (or associated data) to measure radio wave reflection signal 784. Reflection processor 740 may include a reflection coefficient calculator 742 that calculates the S11 reflection coefficient for input radio waves 780 and reflected radio waves 782. The S11 reflection coefficient is the complex ratio of reflected radio waves 782 to input radio waves 780. Reflection processor 740 may utilize methods and/or circuitry known in the art to calculate the S11 reflection coefficient.

In one embodiment, radio-wave analyzer is implemented with a network analyzer, a vector network analyzer, or a chip-based vector network analyzer. Without departing from the scope hereof, radio-wave analyzer 710 may implement radio-wave generator 720, receiver 730, and reflection processor 740 in a manner different from that shown in FIG. 7. For example, receiver 730 may be integrated with radio-wave generator 720, and/or reflection processor 740 may be integrated with receiver 730.

In an embodiment, radio-wave analyzer 710 includes a frequency control unit 750 communicatively coupled with radio-wave generator 720. Frequency control unit 750 controls the frequency of input radio waves 780. In one implementation, frequency control unit 750 is configured to scan the frequency of input radio waves 780. In another implementation, frequency control unit 750 is configured to generate input radio waves 780 at a plurality of different frequencies. In this embodiment, receiver 730 is configured to detect reflected radio waves 782 at least at the frequencies specified by frequency control unit 750, and reflection processor 740 is configured to process input radio waves (or associated data) and reflected radio waves 782 (or associated data) for these frequencies.

In certain embodiments, radio-wave analyzer 710 further includes a calibration unit 744 and probe calibration data 760. Calibration unit 744 is implemented in reflection processor 740. Reflection processor 740 invokes calibration unit 744 to correct radio wave reflection signal 784 according to account for probe calibration data 760. Probe calibration data 760 includes calibration data for coaxial probe 110, such as (a) an open radio-wave reflection signal 762 acquired with coaxial probe 110 interrogating air only, (b) a short radio-wave reflection signal 764 acquired with open end 112 electrically shorted, and/or (c) a liquid radio-wave reflection signal 766 acquired with coaxial probe 110 interrogating a liquid only. Radio-wave analyzer 710 may measure probe calibration data 760. In one example, radio-wave analyzer 710 measures all of open radio-wave reflection signal 762, short radio-wave reflection signal 764, and liquid radio-wave reflection signal 766, prior to storing these to probe calibration data 760, and prior to measuring radio wave reflection signal 784 associated with wine 160.

Processing unit 770 includes a composite property calculator 772. Composite property calculator 772 determines a composite dielectric property for wine 160, bottle 170, and, if applicable, any other intervening medium between open end 112 and wine 160. In one embodiment, processing unit 770 outputs this composite dielectric property as dielectric property 140. Composite property calculator 772 may utilize methods and/or circuitry known in the art to determine the composite dielectric property.

In another embodiment, processing unit 770 further includes extrinsic calibration data 774 and a wine property calculator 778. Wine property calculator 778 utilizes extrinsic calibration data 774 to deduce, from the composite dielectric property determined by composite property calculator 772, a dielectric property of wine 160 alone. In this embodiment, processing unit 770 may output, as dielectric property 140, (a) the dielectric property of wine 160 alone, (b) the composite dielectric property and the dielectric property of wine 160 alone, or (c) the composite dielectric property.

In one example, extrinsic calibration data 774 includes a prior measured value 775 of the composite dielectric property. Prior measured value 775 is obtained for the same bottle of wine currently under testing, or for a similar bottle of wine. For example, prior measured value 775 may be obtained for another bottle of wine having same or similar properties of bottle 170. In another example, extrinsic calibration data 774 includes a dielectric property 776 of bottle 170. In yet another example, extrinsic calibration data 774 includes prior measured value 775 and dielectric property 776 of bottle 170.

Figure 8:
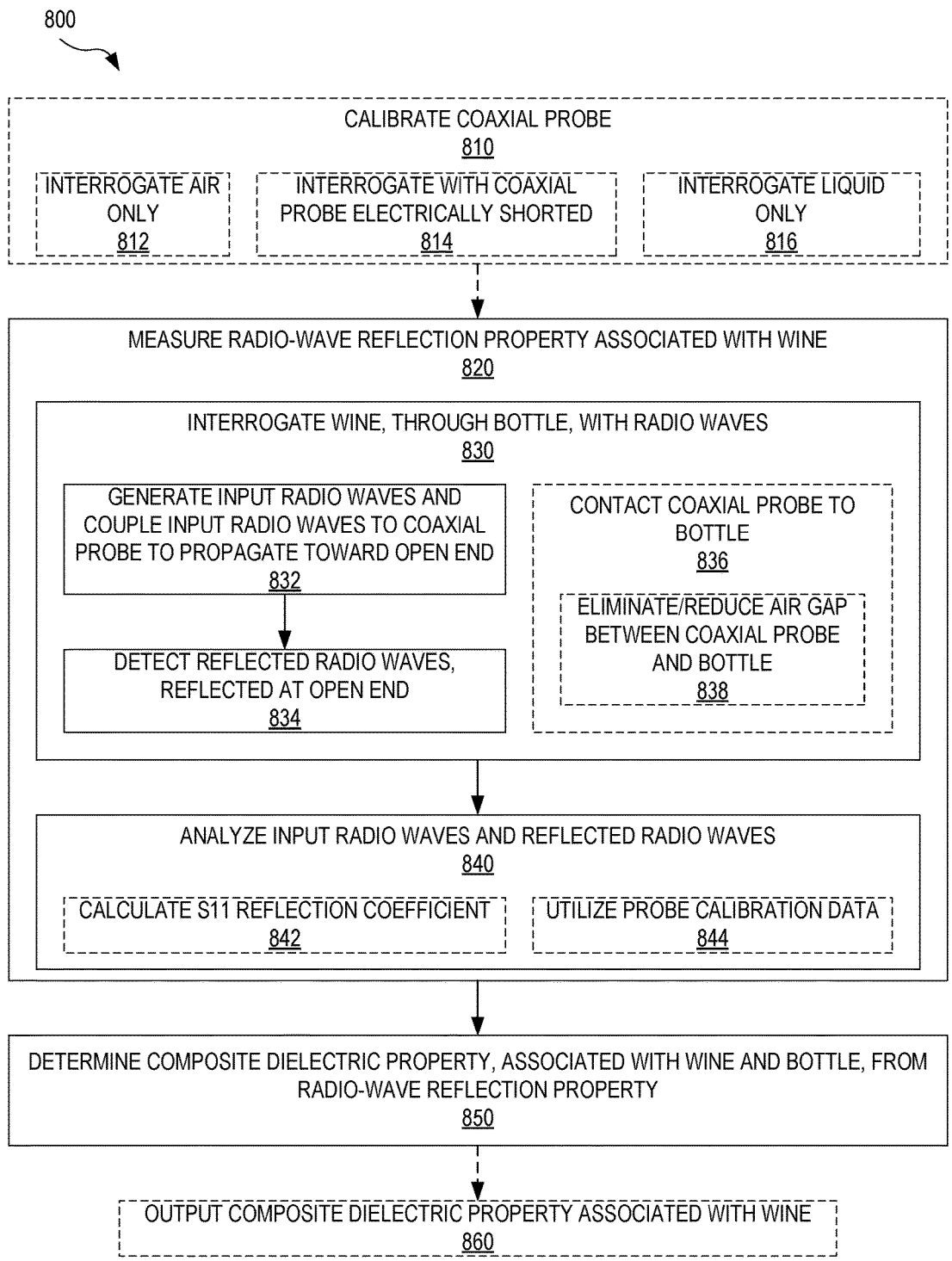
FIG. 8 illustrates a method for dielectric testing of wine in a bottle to determine a composite dielectric property of the wine and the bottle, according to an embodiment.

FIG. 8 illustrates one exemplary method 800 for dielectric testing of wine 160 in bottle 170 to determine a composite dielectric property of wine 160 and bottle 170. Method 800 is an embodiment of method 300 (FIG. 3). Method 800 may be performed by system 700 (FIG. 7), for example with coaxial probe 110 implemented as one of the embodiments shown in FIGS. 2A, 2B, 4, 5, 6A, 6B, 7, and 10.

In a step 820, method 800 measures a radio-wave reflection signal associated with wine 160. Step 820 is an embodiment of step 310 of method 300. In one example of step 820, radio-wave analyzer 710 measures radio-wave reflection signal 784. Radio-wave analyzer 710 may utilize frequency control unit 750 to perform the measurement at a plurality of different radio-wave frequencies. Step 820 includes steps 830 and 840.

In step 830, method 800 uses coaxial probe 110 to interrogate wine 160, through bottle 170, with radio waves 130. Step 830 includes steps 832 and 834. In step 832, input radio waves are generated and coupled to coaxial probe 110 to propagate toward open end 112 of coaxial probe 110. In one example of step 832, radio-wave generator 720 generates input radio waves 780 and couples these to coaxial probe 110. Input radio waves 780 propagate through coaxial probe toward open end 112. In step 834, method 800 detects reflected radio waves that are the reflection of the input radio waves at open end 112. In one example of step 834, receiver 730 detects reflected radio waves 782. Steps 832 and 834 may be performed for a plurality of frequencies of input radio waves 780. In one such example, frequency control unit 750 scans the frequency of input radio waves 780, and receiver 730 detects reflected radio waves 782 for each frequency in the scan. In another such example, frequency control unit 750 generates input radio waves 780 at a plurality of different frequencies, such as two or more different frequencies, and receiver 730 detects reflected radio waves 782 for each such frequency.

In one embodiment of step 832, input radio waves 780 are of a single frequency in the range between 10 MHz and 2 GHz. In another embodiment of step 832, input radio waves 780 are of a single frequency in the range between 50 and 300 MHz. In yet another embodiment of step 832, input radio waves 780 includes radio waves of multiple different frequencies in the range between 10 MHz and 2 GHz or in the range between 50 and 300 MHz. In a further embodiment, the frequency of input radio waves 780 is scanned over a range that includes the range between 50 and 300 MHz or the range between 10 MHz and 1 GHz.

Although shown in FIG. 8 as being performed in series, method 800 may perform steps 832 and 834 in parallel without departing from the scope hereof.

Step 820 may further include a step 836 of contacting coaxial probe 110 to bottle 170. In one example of step 836, coaxial probe 110 is placed as close as possible to wine 160, such that open end 112 contacts bottle 170. Step 836 serves to maximize the distance with which the radio waves propagate into wine 160, to maximize effect of contribution of wine 160 on the measured radio-wave reflection signal. Step 836 may include a step 838 of eliminating or reducing an air gap between coaxial probe 110 and bottle 170. Step 836 serves to minimize the effect of an air gap on the measured radio-wave reflection signal. In one example of step 838, method 800 utilizes a coaxial probe 110 implemented with a curved open end to reduce or eliminate the air gap between coaxial probe 110 and bottle 170. For example, method 800 may utilize one of coaxial probes 400, 500, 600, or 1000 to reduce or eliminate the air gap between coaxial probe 110 and bottle 170.

In step 840, method 800 analyzes the input radio waves of step 832 and the reflected radio waves of step 834 to obtain a measurement of the radio-wave reflection signal for each radio-wave frequency used in step 830. Step 840 may utilize methods known in the art. In one example of step 840, reflection processor 740 analyzes input radio waves 780 (or associated data) and reflected radio waves 782 (or associated data) to obtain radio-wave reflection signal 784. In certain embodiments, step 840 includes a step 842 of calculating the S11 reflection coefficient. Step 842 may utilize methods known in the art to calculate the S11 reflection coefficient from the input radio waves of step 832 and the reflected radio waves of step 834. In one example of step 842, reflection processor 740 uses reflection coefficient calculator 742 to calculate the S11 reflection coefficient.

In an embodiment, step 840 includes a step 844 of utilizing probe calibration data to correct the measured radio-wave reflection signal. In one example of step 844, reflection processor 740 uses calibration unit 744 to correct radio-wave reflection signal 784 according to probe calibration data 760. Step 844 may use a different set of probe calibration data 760 for each radio-wave frequency considered in step 840, if more than one radio-wave frequency is considered. Step 840 may implement both of steps 842 and 844 to take into account probe calibration data 760 when calculating the S11 reflection coefficient.

In a step 850, method 800 determines a composite dielectric property associated with wine 160 and bottle 170 for each radio-wave frequency used in step 830. Step 850 is an embodiment of step 320 of method 300. In one example of step 850, composite property calculator 772 processes radio-wave reflection signal 784 to determine a composite dielectric property of wine 160, bottle 170, and, if applicable, any intervening medium between open end 112 and bottle 170. Step 850 may utilize methods known in the art to compute the composite dielectric property from the radio-wave reflection signal. In one example, open end 112 is curved but step 850 assumes that open end 112 planar. It has been found that this assumption provides valid results for the composite dielectric property.

Optionally, method 800 further includes a step 860 of outputting the composite dielectric property determined in step 850. Step 860 is an embodiment of step 330 of method 300. In one example of step 860, processing unit 770 outputs the composite dielectric property determined in step 850 as dielectric property 140.

In one embodiment, method 800 includes a step 810 of calibrating coaxial probe 110. In one example of step 810, radio-wave analyzer 710 measures radio-wave reflection signal 784 under at least one calibration condition and stores the resulting radio-wave reflection signal 784 for each calibration condition to probe calibration data 760. Step 810 may include one, two, or all of steps 812, 814, and 816. In step 812, coaxial probe 110 is calibrated while interrogating air only. In one example of step 812, radio-wave analyzer 710 measures radio-wave reflection signal 784 when coaxial probe 110 interrogates air only. Radio-wave analyzer 710 stores this value of radio-wave reflection signal 784 to open radio-wave reflection signal 762. In step 814, coaxial probe 110 is calibrated with open end 112 electrically shorted. In one example of step 814, radio-wave analyzer 710 measures radio-wave reflection signal 784 while inner conductor 214 (FIGS. 2A and 2B) is electrically shorted to outer conductor 216. Radio-wave analyzer 710 stores this value of radio-wave reflection signal 784 to short radio-wave reflection signal 764. In step 816, coaxial probe 110 is calibrated while interrogating a calibration liquid only. The calibration liquid is, for example, an alcohol such as ethanol. In one example of step 816, radio-wave analyzer 710 measures radio-wave reflection signal 784 when coaxial probe 110 interrogates the calibration liquid only. Radio-wave analyzer 710 stores this value of radio-wave reflection signal 784 to liquid radio-wave reflection signal 766.

Method 800 may perform step 810 for a plurality of radio-wave frequencies or a range of radio-wave frequencies to generate frequency-dependent probe calibration data for use in embodiments of method 800 that, in step 820, measures the radio-wave reflection signal for a plurality of radio-wave frequencies or a range of radio-wave frequencies.

Figure 9:
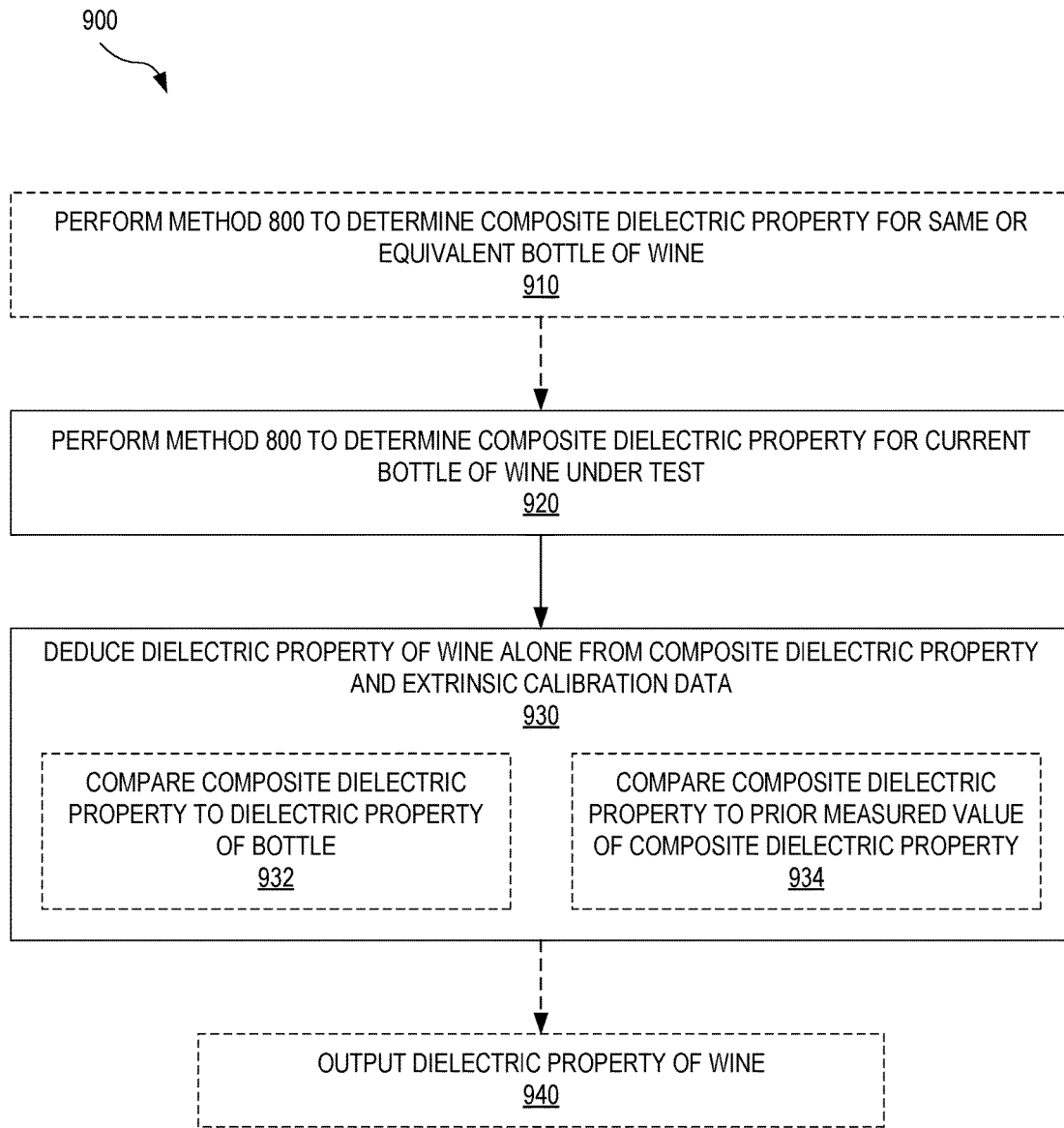
FIG. 9 illustrates a method for dielectric testing of wine in a bottle to determine a dielectric property of the wine alone, according to an embodiment.

FIG. 9 illustrates one exemplary method 900 for dielectric testing of wine 160 in bottle 170 to determine a dielectric property 140 of wine 160 alone. Method 900 is an embodiment of method 300 (FIG. 3) that determines a dielectric property 140 of wine 160 alone. Method 900 may be performed by system 700 (FIG. 7). In the following, method 900 is discussed in the context of a single radio-wave frequency. Without departing from the scope hereof, method 900 may be performed for a plurality or a range of radio-wave frequencies.

In a step 920, method 900 performs method 800 to determine the composite dielectric property of wine 160, bottle 170, and, if applicable, any intervening medium between open end 112 of coaxial probe 110 and bottle 170. In one example of step 920, system 700 performs method 800 to determine the composite dielectric property.

In a step 930, method 900 deduces a dielectric property of wine 160 alone from (a) the composite dielectric property determined in step 920 and (b) extrinsic calibration data. In one implementation, the extrinsic calibration data may include a prior measured value of the composite dielectric property, wherein the prior measured value is obtained for the same bottle of wine tested in step 920, or for a similar bottle of wine. For example, the prior measured value may be obtained for another bottle of wine having same or similar properties of bottle 170. In another implementation, the extrinsic calibration data includes a dielectric property of bottle 170. In yet another implementation, the extrinsic calibration data includes a prior measured value, as discussed above, and a dielectric property of bottle 170.

In one embodiment, step 930 includes a step 932. In step 932, method 900 compares the composite dielectric property determined in step 920 to a known value of the corresponding dielectric property of bottle 170 to determine the corresponding dielectric property of wine 160 alone. In one example of step 932, wine property calculator 778 retrieves dielectric property 776 of bottle 170 from extrinsic calibration data 774. Using this knowledge of dielectric property 776 of bottle 170, wine property calculator 778 deduces, from the composite dielectric property determined in step 920, the corresponding dielectric property of wine 160 alone.

In another embodiment, step 930 includes a step 934. In step 934, method 900 compares the composite dielectric property determined in step 920 to a prior measured value of the same composite dielectric property for the same bottle of wine tested in step 920, or for a similar bottle of wine. In one example of step 934, wine property calculator 778 retrieves prior measured value 775 from extrinsic calibration data 774, and determines the difference between prior measured value 775 and the composite dielectric property determined in step 920. This difference is attributed to a change in a dielectric property of wine 160 alone. In this example, the deduced dielectric property of wine 160 alone is the dielectric property change of wine 160 alone, as determined by wine property calculator 778.

Embodiments of method 900, which include step 934, may further include a step 910 of obtaining the prior measured value of the composite dielectric property. Step 910 is similar to step 920 but is performed before step 920, on either the same bottle of wine or a similar bottle of wine, to obtain a prior measured value of the composite dielectric property. In one example of step 910, system 700 performs method 800 to determine the composite dielectric property and stores this composite dielectric property to extrinsic calibration data 774 as prior measured value 775.

In an optional step 940, method 900 outputs the dielectric property of wine 160 alone. In one example of step 940, wine property calculator 778 outputs a dielectric property of wine 160 alone, or a change thereof, as dielectric property 140.

Figure 10:
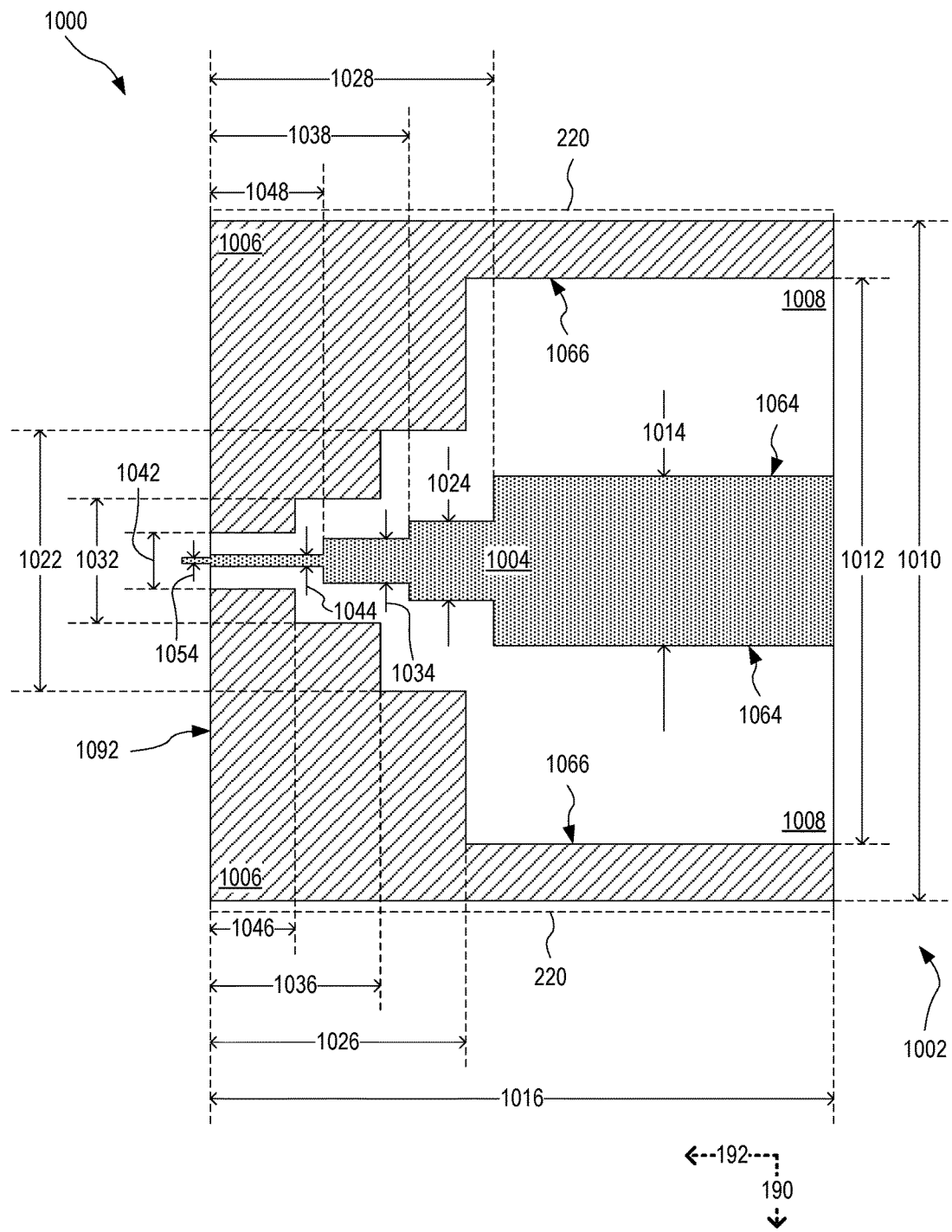
FIG. 10 illustrates an open-ended coaxial probe, for radio-wave interrogation of wine through a bottle, which has a stepped-down probe diameter, according to an embodiment.

FIG. 10 illustrates one exemplary open-ended coaxial probe 1000, for radio-wave interrogation of wine 160 through bottle 170, which has a stepped-down diameter to simultaneously achieve sufficient penetration depth into wine 160 and convenient connection to measurement module 120. Coaxial probe 1000 is configured to impedance match the input impedance of measurement module 120. FIG. 10 shows coaxial probe 1000 in a cross-sectional view, wherein the cross section is taken in the plane spanned by directions 190 and 192.

Coaxial probe 1000 is an embodiment of coaxial probe 110 and has an open end 1002 that is an embodiment of open end 112. Although not shown in the cross-sectional view of FIG. 10, open end 1002 is curved, for example as discussed above in reference to FIG. 4 or FIGS. 6A and 6B. Coaxial probe 1000 includes an inner conductor 1004, an outer conductor 1006, and a dielectric insulator 1008 disposed between inner conductor 1004 and outer conductor 1006. Open end 1002 includes an end face of inner conductor 1004 and an end face of outer conductor 1006. Coaxial probe 1000 may also include insulating jacket 220.

At open end 1002, outer conductor 1006 has an inner diameter 1012 sufficiently large that penetration depth of radio waves 130, away from open end 1002 in the direction toward wine 160, is sufficient to extend through bottle 170 into wine 160 for a bottle 170 having a typical wall-thickness 172 in the range from 2.0 to 3.5 millimeters. In an embodiment, inner diameter 1012 is around 2.0 inches.

At end face 1092, opposite open end 1002, outer conductor 1006 has an inner diameter 1042 and inner conductor 1004 has an outer diameter 1044. Protruding from end face 1092 is a portion of inner conductor 1004 with outer diameter 1054. Inner diameter 1042 and outer diameter 1054 are configured for simple coupling to measurement module 120. In one implementation, inner diameter 1042 and outer diameter 1054 are compatible with connection to a standard radio-frequency coaxial cable connector such as a BNC (Bayonet Neill-Concelman) connector, a TNC (Threaded Neill-Concelman) connector, a Type N connector, an SMA (SubMiniature version A) connector, an SMB (SubMiniature version B) connector, or an SMC (SubMiniature version C) connector. In an embodiment, outer diameter 1054 is around 0.036 inches and inner diameter 1042 is around 0.225.

The inner diameter of outer conductor 1006 and the outer diameter of inner conductor 1004 are increased in a stepwise fashion from end face 1092 to open end 1002. Along direction 192, the ratio of the inner diameter of outer conductor 1006 to the outer diameter of inner conductor 1004 is substantially constant, except for in a small region around each stepwise diameter change. By maintaining a substantially constant ratio between the inner diameter of outer conductor 1006 and the outer diameter of inner conductor 1004, the characteristic impedance of coaxial probe 1000 remains constant along direction 192. In certain embodiments, this characteristic impedance matches the input impedance of measurement module 120. In one such embodiment, the characteristic impedance of coaxial probe 1000 is in the range from 40 to 100 Ohms to match a common input impedance value of a radio-wave analyzer such as a network analyzer or a vector network analyzer. For example, the characteristic impedance of coaxial probe 1000 may be 50 Ohms or 75 Ohms.

In the embodiment shown in FIG. 10, coaxial probe 1000 undergoes three stepwise diameter changes between end face 1092 and open end 1002. Without departing from the scope hereof, the number of such stepwise diameter changes may be smaller or larger than three.

Referring now to the specific embodiment shown in FIG. 10, for a distance 1046 from end face 1092 into coaxial probe 1000 in the negative direction 192, outer conductor 1006 has inner diameter 1042. Extending from distance 1046 to a distance 1036, outer conductor 1006 has inner diameter 1032. Extending from distance 1036 to a distance 1026, outer conductor 1006 has inner diameter 1022. Extending from distance 1026 to a distance 1016, outer conductor 1006 has inner diameter 1012. Distance 1016 is the distance from end face 1092 to open end 1002. Distances 1036 and 1026 are measured from end face 1092. For a distance 1048 from end face 1092 into coaxial probe 1000 in the negative direction 192, inner conductor 1004 has outer diameter 1044. Extending from distance 1048 to a distance 1038, inner conductor 1004 has outer diameter 1034. Extending from distance 1038 to a distance 1028, inner conductor 1004 has outer diameter 1024. Extending from distance 1028 to distance 1016, inner conductor 1004 has outer diameter 1014. Distances 1038 and 1028 are measured from end face 1092.

In one example, approximate values for distances 1046, 1036, 1026, and 1016 are 0.3 inches, 0.6 inches, 0.9 inches, and 2.2 inches, respectively; approximate values for inner diameters 1042, 1032, 1022, and 1012 are 0.225 inches, 0.45 inches, 0.9 inches, and 2.0 inches, respectively; approximate values for distances 1048, 1038, and 1028 are 0.4 inches, 0.7 inches, and 1.0 inches, respectively; approximate values for outer diameters 1054, 1044, 1034, 1024, and 1014 are 0.036 inches, 0.065 inches, 0.131 inches, 0.261 inches, and 0.581 inches, respectively, and outer conductor 1006 has an outer diameter 1010 of approximately 2.4 inches.

Without departing from the scope hereof, the ratio of distance 1016 to inner diameter 1012 may be different from that shown in FIG. 10. For example, the ratio of distance 1016 to inner diameter 1012 may be much greater than that shown in FIG. 10, such that coaxial probe 1000 has length along direction 192 much greater than the maximum value of the inner diameter of outer conductor 1006.

Although FIG. 10 shows outer conductor 1006 as having constant outer diameter 1010 along distance 1016, the outer diameter of outer conductor 1006 may vary with distance 1016, without departing from the scope hereof. In one such example, the outer diameter of outer conductor 1006 undergoes a stepwise change similar to that of the inner diameter of outer conductor 1006.

In one embodiment, inner conductor 1004 is solid metal, for example solid copper with or without additional metal plating as discussed in reference to FIG. 1. In another embodiment, inner conductor 1004 is a metal plated plastic, for example copper plated plastic, wherein the metal plating is on (a) the outer surface 1064 of inner conductor 1004 for the full length of inner conductor 1004 along direction 192 and (b) the surface of the portion of inner conductor 1004 protruding from end face 1092 and having outer diameter 1054. Optionally, this metal plating extends onto a portion of open end 1002 associated with inner conductor 1004. In one embodiment, outer conductor 1006 is solid metal, for example solid copper with or without additional metal plating as discussed in reference to FIG. 1. In another embodiment, outer conductor 1006 is a metal plated plastic, for example copper plated plastic, wherein the metal plating is on the inner surface 1066 of outer conductor 1006 for the full length of outer conductor 1006 along direction 192. Optionally, this metal plating extends onto a portion of end face 1092 associated with outer conductor 1006 and/or a portion of open end 1002 associated with outer conductor 1006. In one embodiment, dielectric insulator 1008 is solid polyethylene, polytetrafluoroethylene, and/or a derivative thereof. In another embodiment, dielectric insulator 1008 is plastic, foam plastic, air (or other gaseous medium) with spacers supporting inner conductor 1004, and/or a combination thereof.

Example I: Dielectric Testing of Water/Ethanol Mixtures

Figure 11:
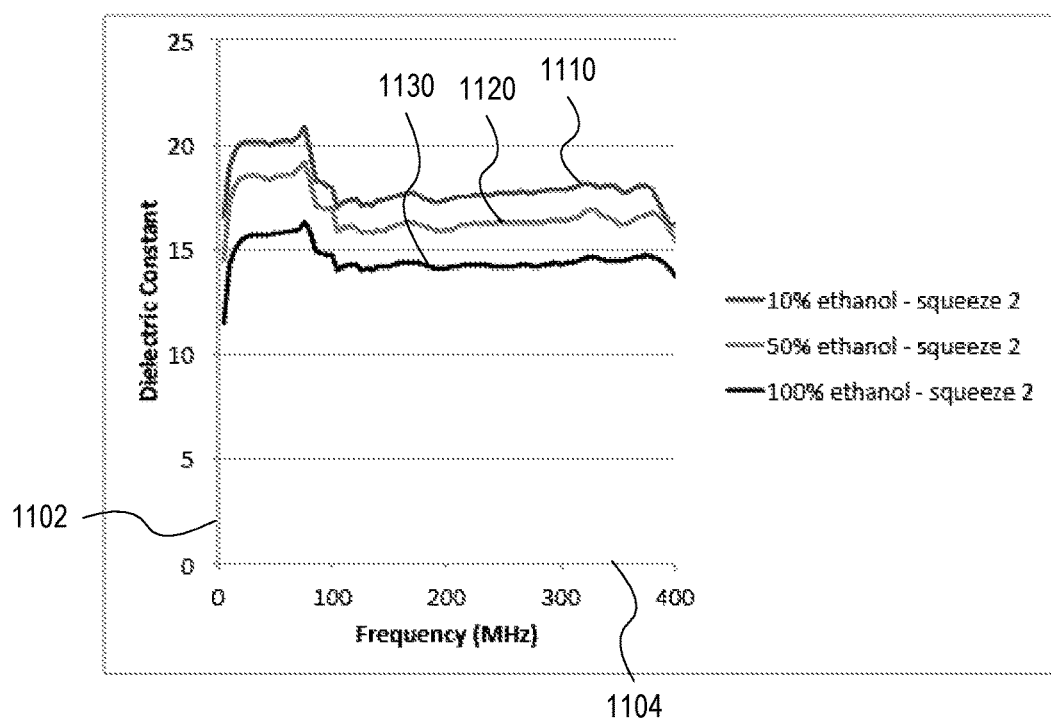
FIG. 11 shows dielectric data for water/ethanol mixtures obtained by performing an embodiment of the method of FIG. 8, using an embodiment of the open-ended coaxial probe of FIG. 4 implemented in an embodiment of the system of FIG. 7.

In this Example, an embodiment of coaxial probe 400 (FIG. 4) is implemented in an embodiment of system 700 to determine dielectric properties of water/ethanol mixtures, an example of wine 160 (FIG. 1). FIG. 11 shows data achieved when the coaxial probe interrogates water/ethanol mixtures through a plastic bottle (an example of bottle 170) containing these water/ethanol mixtures.

The coaxial probe, used in Example I, is fabricated from a commercially available coaxial cable (LMR-1700 from Times Microwave Systems). The coaxial cable is modified to form cylindrically curved open end 410 with radius of curvature of 1.55 inches, matching the radius of the plastic bottle holding the water/ethanol mixtures. The outer conductor (an example of outer conductor 216) is made of copper and has an inner diameter of 1.350 inches and an outer diameter of 1.40 inches. The inner conductor (an example of inner conductor 214) is made of copper and has an outer diameter of 0.527 inches. The inner and outer conductors are spaced apart by a dielectric insulator (and example of dielectric insulator 218) made of polytetrafluoroethylene (Teflon). The coaxial probe includes a rubber covering (an example of insulating jacket 220) having an outer diameter of 1.67 inches.

The coaxial probe is communicatively coupled with a vector network analyzer (Keysight E5071B (Agilent)). This network analyzer is an embodiment of radio-wave analyzer 710 (FIG. 7), implemented with frequency control unit 750, reflection coefficient calculator 742, calibration unit 744, and probe calibration data 760. The vector network analyzer measures and outputs the S11 reflection coefficient (an example of radio-wave reflection signal 784) for radio waves reflected at the open end of the coaxial probe. The vector network analyzer is communicatively coupled with a computer that is equipped with software for determining dielectric properties from the S11 reflection coefficient. This computer is an embodiment of processing unit 770. The software is a portion of the Keysight 85070E Dielectric Probe Kit. This software assumes that the coaxial probe has a planar open end. However, the software was found to generate valid data for dielectric properties of the water/ethanol mixtures even though the software, as implemented in this Example, processes reflection data obtained using a coaxial probe with a curved open end.

FIG. 11 shows the obtained using the system discussed in the preceding paragraphs of Example I, wherein the open end of the coaxial probe interrogates the water/ethanol mixtures through a plastic bottle. The data of FIG. 11 is obtained by performing an embodiment of method 800 (FIG. 8). The coaxial probe is calibrated according to step 810, implemented with steps 812, 814, and 816. The resulting calibration data is stored to probe calibration data 760 and utilized by the vector network analyzer when calculating the S11 reflection coefficient in step 840.

The composite real relative permittivity 1102 of the water/ethanol mixture and the plastic bottle is determined at radio-wave frequencies 1104 in the range from 10 to 400 MHz for three different liquids: 10% ethanol/90% water (see curve 1110), 50% ethanol/50% water (see curve 1120), and 100% ethanol (see curve 1130). It is clear from curves 1110, 1120, and 1130 that the composite real relative permittivity, at each radio-wave frequency evaluated and as determined using the present system, probe, and method, is capable of distinguishing between different ethanol concentrations. The feature in the frequency range below about 100 MHz is believed to be caused by an experimental imperfection. The drop in composite real relative permittivity at around 380 MHz may be due to a "breakdown" of propagation modes through the coaxial probe. At low radio-wave frequencies, the radio waves propagate through the coaxial probe as transverse electromagnetic (TEM) mode radio waves. However, at greater radio-wave frequencies, due to the relatively large inner diameter of the outer conductor, the radio waves begin to propagate as non-TEM mode radio waves, resulting in the "breakdown". It is possible that this breakdown happens at about 380 MHz, thereby causing the drop in composite real relative permittivity. Alternatively, the breakdown frequency is greater than 380 MHz and the drop in composite real relative permittivity is caused by an experimental imperfection. However, in the range between about 100 MHz and about 380 MHz, the composite real relative permittivity is relatively constant. This illustrates that the composite real relative permittivity exhibits predominantly broadband behavior, at least in the range between about 100 MHz and about 380 MHz. Thus, for such mixtures it would likely be sufficient to measure the composite real relative permittivity at a single radio-wave frequency in the range between about 100 MHz and (a) about 380 MHz or (b) the radio-wave frequency associated with breakdown of propagation modes if this frequency is different from 380 MHz.

Figure 12:
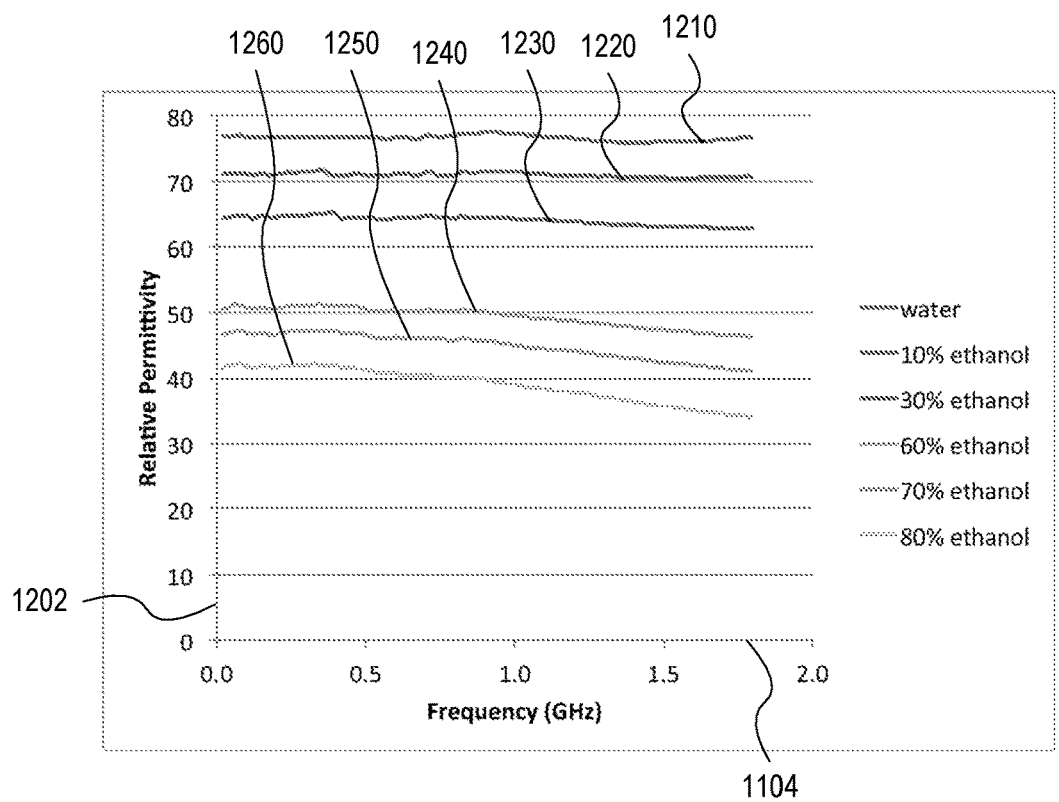
FIG. 12 shows measurements of the relative permittivity of water/ethanol mixtures obtained by directly interrogating the water/ethanol mixtures with an open-ended coaxial probe.

For comparison, FIG. 12 shows the real relative permittivity of water/ethanol mixtures obtained by directly interrogating the water/ethanol mixtures, as opposed to interrogating through bottle 170. The data of FIG. 12 are obtained using the same system and method as used for FIG. 11 except for two modifications: (1) the coaxial probe of FIG. 11 is replaced by the coaxial probe included in the Keysight 85070E Dielectric Probe Kit, and (2) the bottle is eliminated such that the coaxial probe is in direct contact with the water/ethanol mixtures. FIG. 12 shows the real relative permittivity 1202, as a function of radio-wave frequency 1104 in the range from 10 MHz to 1.7 GHz, for six different liquids: 100% water (see curve 1210), 10% ethanol/90% water (see curve 1220), 30% ethanol/70% water (see curve 1230), 60% ethanol/40% water (see curve 1240), 70% ethanol/30% water (see curve 1250), and 80% ethanol/20% water (see curve 1260). The real relative permittivity is relatively constant across the evaluated radio-wave frequency range and shows clear delineation between different ethanol concentrations. The real relative permittivities of these mixtures are generally higher than the composite real relative permittivities shown in FIG. 12. This is due to the fact that the lower real relative permittivity of the bottle contributes to the composite real relative permittivities of FIG. 12.

Combinations of Features

Features described above as well as those claimed below may be combined in various ways without departing from the scope hereof. For example, it will be appreciated that aspects of one system, probe, or method for dielectric testing of wine in a bottle described herein may incorporate or swap features of another system, probe, or method for dielectric testing of wine in a bottle described herein. The following examples illustrate some possible, non-limiting combinations of embodiments described above. It should be clear that many other changes and modifications may be made to the methods and device herein without departing from the spirit and scope of this invention:

(A1) A system for dielectric testing of wine in a bottle may include (a) a coaxial probe for interrogating the wine, wherein the coaxial probe has an open end for contacting an exterior surface of the bottle, and (b) a measurement module for determining a dielectric property associated with the wine by generating and measuring radio waves propagating through the coaxial cable.

(A2) In the system denoted as (A1), the dielectric property may be the real part of permittivity of at least one of (i) the wine and (ii) the wine and portion of the bottle interrogated by the coaxial probe.

(A3) In the system denoted as (A1), the dielectric property may be the imaginary part of permittivity of at least one of (i) the wine and (ii) the wine and portion of the bottle interrogated by the coaxial probe.

(A4) In any of the systems denoted as (A1) through (A3), the measurement module may include a radio-wave analyzer for generating input radio waves propagating through the coaxial probe toward the open end and measuring reflected radio waves (produced at the open end from the input radio waves) to measure a radio-wave reflection signal, and a processing unit for processing the radio-wave reflection signal to determine the dielectric property.

(A5) In the system denoted as (A4), the radio-wave analyzer may include a frequency control unit for generating the input radio waves at a plurality of frequencies, and the processing unit may be configured to determine the dielectric property for each of the plurality of frequencies.

(A6) In the system denoted as (A5), the plurality of frequencies may be in the range between 10 megahertz and 2 gigahertz.

(A7) In the system denoted as (A5), the plurality of frequencies may be a frequency scan including the range from 50 to 300 megahertz.

(A8) In any of the systems denoted as (A4) through (A7), the radio-wave analyzer may include a reflection coefficient calculator for calculating a reflection coefficient based upon the input radio waves and the reflected radio waves.

(A9) In the system denoted as (A8), the reflection coefficient may be the S11 reflection coefficient for transverse electromagnetic mode radio waves.

(A10) In any of the systems denoted as (A4) through (A9), the processing unit may include (a) a composite property calculator for processing the radio-wave reflection signal to determine a composite dielectric property of the wine and portion of the bottle interrogated by the coaxial probe, (b) extrinsic calibration data selected from the group consisting of prior measured value of the composite dielectric property, dielectric property of the bottle, and a combination thereof, and (c) a wine property calculator for comparing the composite dielectric property to the extrinsic calibration data to deduce a property of the wine alone.

(A11) In the system denoted as (A10), the property of the wine alone may be a dielectric property of the wine alone.

(A12) In either or both of the systems denoted as (A10) and (A11), the calibration data may include a dielectric property of a certain type of bottle.

(A13) In any of the systems denoted as (A10) through (A12), the calibration data may include prior measurement of the composite dielectric property.

(A14) In any of the systems denoted as (A4) through (A13), the radio-wave analyzer may include (a) probe calibration data including (i) an open radio-wave reflection signal acquired with the coaxial probe interrogating air only, (ii) a short radio-wave reflection signal acquired with the open end electrically shorted, and (iii) a liquid radio-wave reflection signal acquired with the coaxial probe interrogating liquid only, and (b) a calibration unit for correcting the radio-wave reflection signal based upon both measurements performed by the radio-wave analyzer and the probe calibration data.

(B1) A method for dielectric testing of wine in a bottle may include measuring a radio-wave reflection signal associated with the wine by interrogating the wine, through the bottle, with radio waves, and determining a dielectric property associated with the wine from the radio-wave reflection signal.

(B2) In the method denoted as (B1), in the step of measuring, the radio waves may include radio waves of frequency in the range between 10 megahertz and 2 gigahertz.

(B3) In the method denoted as (B1), the step of interrogating may include scanning the frequency between 50 and 300 megahertz.

(B4) In any of the methods denoted as (B1) through (B4), the step of interrogating may include propagating the radio waves through a coaxial probe having an open end that interfaces with an exterior surface of the bottle.

(B5) In the method denoted as (B4), the step of interrogating may include contacting the coaxial probe to the exterior surface.

(B6) In the method denoted as (B5), the step of contacting may include eliminating air gap between the open end and the exterior surface.

(B7) In any of the methods denoted as (B4) through (B6), the step of measuring may include analyzing (a) input radio waves propagating through the coaxial probe toward the open end and (b) reflected radio waves produced at the open end from the input radio waves.

(B8) In the method denoted as (B7), the step of analyzing may include calculating the S11 reflection coefficient for transverse electromagnetic mode radio waves.

(B9) In any of the methods denoted as (B4) through (B8), in the step of interrogating, the open end may be curved.

(B10) In the method denoted as (B9), the step of determining may include assuming that the open end is planar.

(B11) In any of the methods denoted as (B1) through (B10), the dielectric property associated with the wine may be a composite dielectric property of the wine and portion of the bottle interrogated by the coaxial probe.

(B12) In any of the methods denoted as (B1) through (B11), the step of determining may include processing the radio-wave reflection signal to determine a composite dielectric property of the wine and portion of the bottle interrogated by the coaxial probe, and deducing a property of the wine alone based upon the composite dielectric property and extrinsic calibration data.

(B13) In the method denoted as (B12), the extrinsic calibration data may be selected from the group consisting of prior measured value of the composite dielectric property, dielectric property of the bottle, and a combination thereof.

(B14) In either of both of the methods denoted as (B12) and (B13), the composite dielectric property may be the real part of permittivity of the wine and the portion of the bottle interrogated by the coaxial probe.

(B15) In either of both of the methods denoted as (B12) and (B13), the composite dielectric property may be the imaginary part of the permittivity of the wine and portion of the bottle interrogated by the coaxial probe.

(B16) In any of the methods denoted as (B12) through (B15), in the step of deducing, the property of the wine alone may be a dielectric property of the wine alone.

(B17) In the method denoted as (B16), in the step of deducing, the dielectric property of the wine alone may be the real part of permittivity of the wine alone.

(B18) In the method denoted as (B16), in the step of deducing, the dielectric property of the wine alone may be the imaginary part of permittivity of the wine alone.

(B19) In the method denoted as (B16), in the step of deducing, the dielectric property of the wine alone may include a relaxation frequency.

(B20) Any of the methods denoted as (B1) through (B19) may further include calibrating the coaxial probe to obtain probe calibration data.

(B21) The method denoted as (B20) may further include, in the step of measuring, correcting the radio-wave reflection signal based upon (a) measurements performed on the wine in the bottle and (b) the probe calibration data.

(B22) In either or both of the methods denoted as (B20) and (B21), the step of calibrating may include acquiring an open radio-wave reflection signal with the coaxial probe interrogating air only, acquiring a short radio-wave reflection signal with the open end electrically shorted, and acquiring a liquid radio-wave reflection signal with the coaxial probe interrogating liquid only.

(C1) A probe for radio-wave interrogation of wine in a bottle may include an inner conductor, an outer conductor, and an open end, wherein the open end includes an end face of the inner conductor and an end face of the outer conductor, and having curvature matching curvature of an exterior surface of the bottle.

(C2) In the probe denoted as (C1), the open end may have radius of curvature in range between 30 and 50 millimeters.

(C3) In either of both of the probes denoted as (C1) and (C2), at the open end, the outer conductor may have inner diameter sufficiently large that radio waves of frequency 300 megahertz have penetration depth away from the open end toward the wine of at least three millimeters.

(C4) In any of the probes denoted as (C1) through (C3), the inner diameter may be at least 45 millimeters.

(C5) In any of the probes denoted as (C1) through (C4), the inner conductor and outer conductor may be coaxial.

(C6) In any of the probes denoted as (C1) through (C5), the inner diameter of the outer conductor may decrease with distance along the coaxial probe away from the open end.

(C7) In any of the probes denoted as (C1) through (C6), the ratio of (a) the inner diameter of the outer conductor to (b) outer diameter of the inner conductor may be independent of the distance.

(C8) In the probe denoted as (C7), the ratio may correspond to a characteristic impedance of the coaxial probe.

(C9) In the probe denote as (C8), the characteristic impedance may be in the range from 40 to 100 Ohms.

(C10) In the probe denoted as (C8), the characteristic impedance of the coaxial probe may be 50 ohms or 75 ohms.

(C11) In any of the probes denoted as (C6) through (C10), the inner diameter may decrease with the distance away from the open end in a stepwise manner.

(C12) In any of the probes denoted as (C1) through (C11), the inner diameter may have minimum value no greater than 10 millimeters.

(C13) In any of the probes denoted as (C1) through (C12), the outer conductor may be spaced from the inner conductor by a dielectric material.

(C14) In any of the probes denoted as (C1) through (C13), the open end may include a deformable, conductive gasket for eliminating non-conductive gap between the open end and the exterior surface.

Changes may be made in the above systems, probes, and methods without departing from the scope hereof. It should thus be noted that the matter contained in the above description and shown in the accompanying drawings should be interpreted as illustrative and not in a limiting sense. The following claims are intended to cover generic and specific features described herein, as well as all statements of the scope of the present systems, probes, and methods, which, as a matter of language, might be said to fall therebetween.

What is claimed is:

1. A probe for radio-wave interrogation of wine in a bottle, comprising:
    an inner conductor;
    an outer conductor coaxial with the inner conductor, the outer conductor being spaced apart from the inner conductor by a dielectric material; and
    a concave open end configured to interface with a convex exterior surface of the bottle during said radio-wave interrogation, the concave open end including an end face of the inner conductor and an end face of the outer conductor, curvature of the concave open end matching curvature of the convex exterior surface.

2. The probe of claim 1, the concave open end having radius of curvature in range between 30 and 50 millimeters.

3. The probe of claim 1, at the concave open end, the outer conductor having inner diameter sufficiently large that radio waves of frequency 300 megahertz have penetration depth away from the open end toward the wine of at least three millimeters.

4. The probe of claim 3, the inner diameter being at least 45 millimeters.

5. The probe of claim 1, inner diameter of the outer conductor decreasing with distance along the probe away from the concave open end.

6. The probe of claim 5, ratio of (a) the inner diameter of the outer conductor to (b) outer diameter of the inner conductor being independent of the distance.

7. The probe of claim 6, the inner diameter decreasing with the distance away from the open end in a stepwise manner.

8. The probe of claim 1, the concave open end including a deformable, conductive gasket for eliminating non-conductive gap between the concave open end and the convex exterior surface.

9. The probe of claim 1, the curvature of the concave open end being cylindrical.

* * * * *